(12) United States Patent
Parsa et al.

(10) Patent No.: US 10,295,488 B2
(45) Date of Patent: May 21, 2019

(54) SENSOR FLUID RESERVOIRS FOR MICROFABRICATED SENSOR CELLS

(71) Applicant: Texas Instruments Incorporated, Dallas, TX (US)

(72) Inventors: Roozbeh Parsa, Portola Valley, CA (US); Nathan Brockie, Edinburgh (GB); Terry Dyer, Largs (GB); William French, San Jose, CA (US); Iouri N Mirgorodski, Sunnyvale, CA (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 410 days.

(21) Appl. No.: 14/993,073

(22) Filed: Jan. 11, 2016

(65) Prior Publication Data
US 2017/0199138 A1    Jul. 13, 2017

(51) Int. Cl.
*G01N 25/02* (2006.01)
*G04F 5/14* (2006.01)
*H03L 7/26* (2006.01)

(52) U.S. Cl.
CPC .............. *G01N 25/02* (2013.01); *G04F 5/14* (2013.01); *H03L 7/26* (2013.01)

(58) Field of Classification Search
CPC .............. G01N 25/02; H03L 7/26; G04F 5/14
USPC ........................................................ 73/61.77
See application file for complete search history.

(56) References Cited

U.S. PATENT DOCUMENTS

| | | | |
|---|---|---|---|
| 6,570,459 B1* | 5/2003 | Nathanson | G04F 5/14 331/94.1 |
| 9,169,974 B2* | 10/2015 | Parsa | F17C 3/00 |
| 9,350,368 B2* | 5/2016 | Maki | H03L 7/26 |
| 9,515,670 B2* | 12/2016 | Ishihara | G04F 5/145 |
| 9,568,565 B2* | 2/2017 | Parsa | G01R 33/032 |
| 9,595,973 B2* | 3/2017 | Ishihara | H03L 7/26 |
| 9,692,432 B2* | 6/2017 | Yoshida | H03L 7/26 |
| 9,755,654 B2* | 9/2017 | Nakajima | H03L 7/26 |
| 9,763,314 B1* | 9/2017 | Roper | H05H 3/02 |
| 2005/0184815 A1* | 8/2005 | Lipp | G04F 5/14 331/94.1 |
| 2008/0278710 A1* | 11/2008 | Schmidt | G01N 21/3103 356/73 |
| 2011/0187464 A1* | 8/2011 | Youngner | G04F 5/14 331/94.1 |

(Continued)

*Primary Examiner* — Nathaniel T Woodward
(74) *Attorney, Agent, or Firm* — Andrew R. Ralston; Charles A. Brill; Frank D. Cimino

(57) ABSTRACT

A sensor cell has a chamber that defines an internal sensor volume for a sensor fluid in a vapor phase. A signal path extends into the internal sensor volume. The sensor cell includes a condensation reservoir for a condensed phase of the sensor fluid, in fluid communication with the internal sensor volume. The signal path is spatially separate from the condensation reservoir. During operation of the sensor cell, some of the sensor fluid may be converted to a vapor phase in the internal sensor volume. During such operation, sensor fluid in the condensed phase is disposed in the condensation reservoir, advantageously out of the signal path, leaving the signal path desirably free of the condensed phase sensor fluid. During periods of non-operation, a significant portion of the sensor fluid may condense from the vapor phase to the condensed phase in the condensation reservoir, advantageously out of the signal path.

31 Claims, 11 Drawing Sheets

(56) References Cited

U.S. PATENT DOCUMENTS

2013/0320567 A1* 12/2013 Thacker ............ H01L 25/0652
257/777
2015/0270843 A1* 9/2015 Nakajima ................ H03L 7/26
331/94.1

* cited by examiner

SENSOR FLUID RESERVOIRS FOR MICROFABRICATED SENSOR CELLS

FIELD

This disclosure relates to the field of sensor cells. More particularly, this disclosure relates to sensor cells with vapor phase sensor fluids.

BACKGROUND

Some sensor cells have sensor fluids that have a desired amount of the sensor fluid in a vapor phase during operation. The sensor cell provides a signal path through which a signal, such as an electromagnetic signal or an acoustic signal, may pass. For instance, a signal can be introduced into and/or received from the sensor cell during operation of the sensor cell and by interacting with the sensor fluid in the vapor phase. The sensor cell is typically heated during operation to provide the desired amount of the sensor fluid in the vapor phase. During inoperative periods, the cell cools, and a large portion of the sensor fluid in the vapor phase condenses into a condensed phase, that is, a liquid and/or a solid phase. Examples of such sensor cells are atomic clocks and magnetometers, which use alkali metals as sensor fluids, and have optical signal paths in the sensor cells. There is great interest in reducing the size and power requirements of such sensor cells, to enable widespread use in low cost, handheld, mobile, and other applications. As the sizes of the sensor cells are reduced, a problem arises in which the sensor fluid in the condensed phase blocks the signal path in the sensor cell. In cases where some of the sensor fluid remains in the condensed phase during operation, for example to ensure attaining the required amount of sensor fluid in the vapor phase, the sensor fluid in the condensed phase undesirably interferes with the signal during operation. In some cases, less sensor fluid is disposed in the sensor cell so as to minimize condensation in the signal path, resulting in substantially all the sensor fluid being in the vapor phase during operation. In these cases, the vapor pressure of the sensor fluid, and hence the amount of sensor fluid in the sensor cell may vary from sensor cell to sensor cell, thereby introducing variation in performance uniformity of the sensor cells.

SUMMARY

The following presents a simplified summary in order to provide a basic understanding of one or more aspects of the disclosure. This summary is not an extensive overview of the disclosure, and is neither intended to identify key or critical elements of the disclosure, nor to delineate the scope thereof. Rather, the primary purpose of the summary is to present some concepts of the disclosure in a simplified form as a prelude to a more detailed description that is presented later.

A sensor cell has a chamber that defines an internal sensor volume for a sensor fluid in a vapor phase. A signal path extends into the internal sensor volume. The sensor cell includes a condensation reservoir for a fluid phase of the sensor fluid. The condensation reservoir is in fluid communication with the internal sensor volume. The signal path is spatially separate from, and does not encompass, the condensation reservoir.

DETAILED DESCRIPTION

Figure 1:
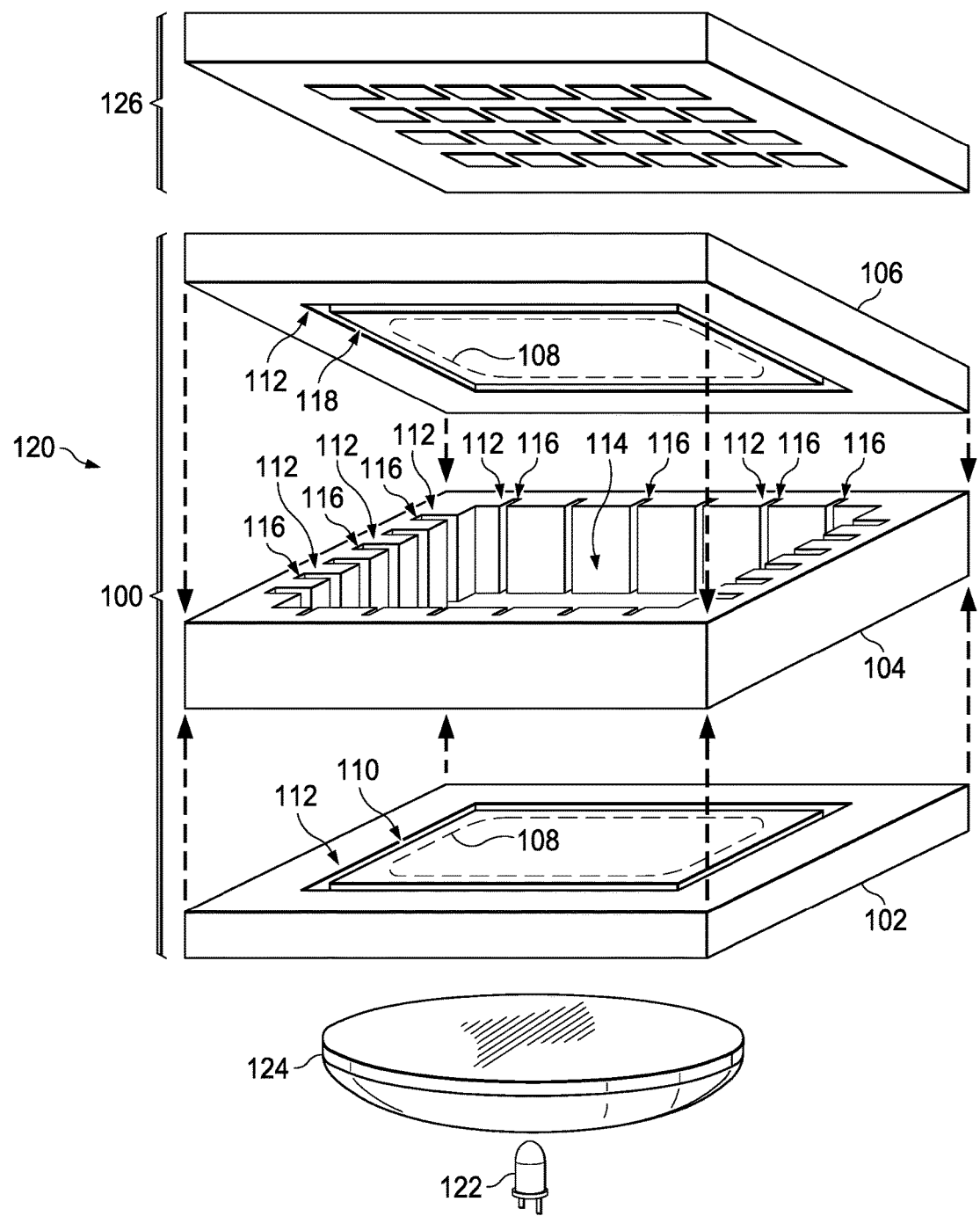
FIG. 1 is an exploded view of an example sensor cell with a condensation reservoir.

The present disclosure is described with reference to the attached figures. The figures are not drawn to scale and they are provided merely to illustrate the disclosure. Several aspects of the disclosure are described below with reference to example applications for illustration. It should be understood that numerous specific details, relationships, and methods are set forth to provide an understanding of the disclosure. One skilled in the relevant art, however, will readily recognize that the disclosure can be practiced without one or more of the specific details or with other methods. In other instances, well-known structures or operations are not shown in detail to avoid obscuring the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

A sensor cell has a chamber that defines an internal sensor volume for a sensor fluid in a vapor phase. A signal path extends into the internal sensor volume. The sensor cell includes a condensation reservoir for a fluid phase of the sensor fluid. The condensation reservoir is in fluid communication with the internal sensor volume. The signal path is spatially separate from the condensation reservoir, that is, the signal path does not encompass the condensation reservoir. The signal path in the internal sensor volume is free of metal conductors for the signal, such as coaxial cables and twisted pair lines.

The condensation reservoir may be manifested as one or more grooves open to the internal sensor volume. Each groove may be less than 1 millimeter wide and less than 5 millimeters deep, so as to hold the sensor fluid in a liquid phase by capillary action. Grooves larger than 1 millimeter wide may not provide adequate capillary action for fluids with surface tension values less than a few hundred dynes/cm$^2$, such as polar fluids and liquid alkali metals like cesium and rubidium.

During operation of the sensor cell, at least a portion, if not all, of the sensor fluid may be converted to a vapor phase, for example by heating the sensor cell, to provide a desired amount of the sensor fluid in the vapor phase for proper operation of the sensor cell. During such operation, sensor fluid in a condensed phase is disposed in the condensation reservoir, advantageously out of the signal path, leaving the signal path desirably free of the condensed phase sensor fluid. At other times, for example during periods when the sensor cell is not operating in a sensing mode, the sensor cell may be cooler than during operation, so that a significant portion of the sensor fluid may condense from the vapor phase to the condensed phase in the condensation reservoir, advantageously out of the signal path. A volume of the condensation reservoir may be at least as large as a total volume of the sensor fluid in the condensed phase, desirably reducing a probability of condensing the sensor fluid in the signal path. Having the condensation reservoir in the sensor cell improves a process latitude for disposing sensor fluid into the internal sensor volume during a process of forming the sensor cell, as a sufficient amount of sensor fluid may be disposed into the sensor cell to provide a saturated vapor of sensor fluid during operation while maintaining the signal path free of the condensed phase sensor fluid. The condensation reservoir accommodates the unavoidable variations in the amount of sensor fluid disposed into sensor cells during a process of forming the sensor cells.

FIG. 1 is an exploded view of an example sensor cell with a condensation reservoir. The sensor cell 100 of the instant example includes a first plate 102, an interposer 104 and a second plate 106, which provide a chamber of the sensor cell 100. The sensor cell 100 is formed by attaching the first plate 102 to the interposer 104 and attaching the second plate 106 to the interposer 104 opposite the first plate 102. A boundary of a signal path 108 is depicted in FIG. 1 by a phantom outline on the first plate 102 and the second plate 106; the signal path 108 extends through the sensor cell 100.

In the instant example, the first plate 102 may comprise an optically transparent material, such as glass, quartz or sapphire, in the signal path 108. In one version of the instant example, the first plate 102 may be formed of the optically transparent material. In another version, the optically transparent material may be confined to the signal path 108, and a remainder of the first plate 102 may comprise a structural material such as silicon, kovar, ceramic, or aluminum. The first plate 102 may have a first groove 110 which is a portion of the condensation reservoir 112. The first groove 110 opens to an internal sensor volume 114 of the sensor cell 100. The first groove 110 is disposed outside of the signal path 108. The first groove 110 may be less than 1 millimeter wide, for example, 50 microns to 200 microns wide. The first groove 110 may be less than 5 millimeters deep. The first groove 110 may be continuous around the signal path 108 as depicted in FIG. 1, or may be segmented.

The interposer 104 may be configured as a closed loop that laterally surrounds the internal sensor volume 114. The signal path 108 extends through the internal sensor volume 114; the interposer 104 lies outside of the signal path 108. The interposer 104 may comprise a structural material which is conducive to fabrication in a closed-loop configuration as depicted in FIG. 1, and to forming desired attachments to the first plate 102 and the second plate 106. Examples of such structural materials are silicon, ceramic, and some metals such as aluminum and kovar. The interposer 104 may have one or more second grooves 116 which are portions of the condensation reservoir 112. The second grooves 116 open to the internal sensor volume 114. The second grooves 116 are disposed outside of the signal path 108. Each of the second grooves 116 may be less than 1 millimeter wide, and may be less than 5 millimeters deep. The second grooves 116 may extend across the interposer 104 from proximate to the first plate 102 to proximate to the second plate 106, and may be distributed around the internal sensor volume 114, as depicted in FIG. 1, or may have another distribution. The interposer 104 may have surfaces surrounding the internal sensor volume 114 which are substantially perpendicular to the first plate 102 and the second plate 106, as depicted in FIG. 1. Alternatively, the surfaces surrounding the internal sensor volume 114 may be sloped, as a result of an etching process used to form the interposer 104.

The second plate 106 may be structurally similar to the first plate 102, as depicted in FIG. 1, or may have a different structure and composition. In the instant example, the signal path 108 extends to, and possibly through, the second plate 106. The second plate 106 may have a third groove 118 which is a portion of the condensation reservoir 112. The third groove 118 opens to the internal sensor volume 114. The third groove 118 is disposed outside of the signal path 108. The third groove 118 may be less than 1 millimeter wide, and may be less than 5 millimeters deep. The third groove 118 may have a similar configuration to the first groove 110 in the first plate 102, or may have a different configuration.

The condensation reservoir 112 comprises the first groove 110, the second grooves 116 and the third groove 118, at least one of which is in the sensor cell 100 of the instant example. The sensor cell 100 may possibly have all of the first groove 110, the second grooves 116 and the third groove 118.

The sensor cell 100 may be part of a sensor system 120 which may include a signal source 122 at one end of the signal path 108 and/or one or more signal conditioning elements 124 in the signal path 108, and includes a signal detector 126 at another end of the signal path 108. The signal source 122 is depicted in FIG. 1 as a light emitting diode (LED), but may be another optical signal source such as a laser or an incandescent source. Alternatively, the signal source 122 may be a microwave source such as a high frequency field effect transistor (HF FET), a tunnel diode (Esaki diode), a Gunn diode, or an impact ionization avalanche transit time (IMPATT) diode. Alternatively, the signal source 122 may be an acoustic source such as a piezoelectric ultrasonic element. Other types of signal sources 122 are within the scope of the instant example. The signal conditioning elements 124 are depicted in FIG. 1 as an optical lens, but may include optical filters, polarizers, mirrors, quarter-wave plates and/or other optical elements. Alternatively, the signal conditioning elements 124 may include microwave filters, microwave polarizers and/or non-linear microwave beam-shaping elements. Other types of signal conditioning elements 124 are within the scope of the instant example. The signal detector 126 is depicted in FIG. 1 as a semiconductor optical signal detector, but may be a bolometer, an image intensifier, a photomultiplier, or other optical signal detector. Alternatively, the signal detector 126 may be a microwave detector using a tunnel diode or a HF FET. Alternatively, the signal detector 126 may be an acoustic detector such as a piezoelectric microphone or an array of microelectronic mechanical system (MEMS) microphones. Other types of signal detector 126 are within the scope of the instant example. The signal path 108 extends from the signal source 122 through the internal sensor volume 114 to the signal detector 126, and does not include the condensation reservoir 112. Although a portion of signal emissions from the signal source 122 may be emitted into a region outside of the signal path 108 and this portion may be blocked or otherwise interfered with by the condensation reservoir 112, it is understood that the signal path 108 excludes path the condensation reservoir 112.

During operation of the sensor system 120, some or all of sensor fluid in the sensor cell 100 may be converted to a vapor phase for proper operation of the sensor system 120. During such operation, the sensor fluid in a condensed phase is disposed in the condensation reservoir 112, advantageously out of the signal path 108, leaving the signal path 108 desirably free of the condensed phase sensor fluid. At other times, a significant portion of the sensor fluid may condense from the vapor phase to the condensed phase in the condensation reservoir 112, advantageously out of the signal path 108.

Figure 2:
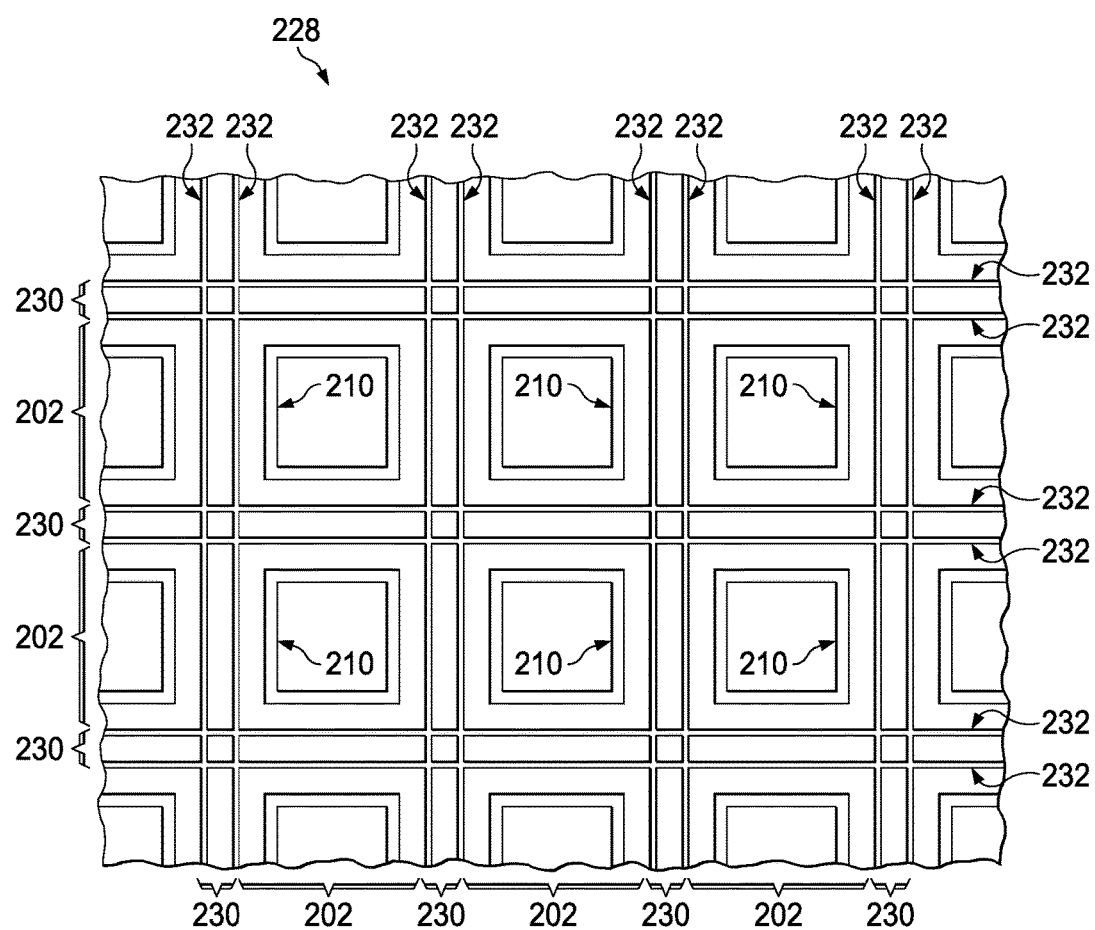
FIG. 2 is a plan view of a plurality of plates similar to the first plate and/or the second plate described in reference to FIG. 1, depicted in an example method of formation.

FIG. 2 is a plan view of a plurality of plates similar to the first plate 102 and/or the second plate 106 described in reference to FIG. 1, depicted in an example method of formation. The plurality of plates 202 are contained in a workpiece 228, which may be, for example, a circular wafer of glass, sapphire, or quartz, compatible with semiconductor processing equipment. Alternatively, the workpiece 228 may be a square or rectangular substrate of ceramic or metal, compatible with chip carrier processing equipment. The instances of the plates 202 are arranged in rows and columns, separated by singulation lanes 230. Condensation reservoir grooves 210 are formed in the plates 202 to be part of condensation reservoirs of sensor cells containing the plates 202. The condensation reservoir grooves 210 may be formed sequentially in each plate 202 or may be formed concurrently in all the plates 202, depending on the method of forming the condensation reservoir grooves 210. The condensation reservoir grooves 210 may have a continuous configuration as depicted in FIG. 2, or may have a segmented configuration. In the instant example, optional singulation assist grooves 232 may be formed in the workpiece 228 in the singulation lanes 230. The singulation assist grooves 232 are formed by the same process used to form the condensation reservoir grooves 210. The plates 202 are subsequently separated from each other by a singulation process such as sawing, mechanical scribing, or laser scribing, through the singulation lanes 230. The singulation assist grooves 232 may advantageously reduce crack propagation from the singulation process into the plates 202. Forming the plates 202 in the workpiece 228 may advantageously reduce fabrication costs of the sensor cells containing the plates 202.

Figure 3:
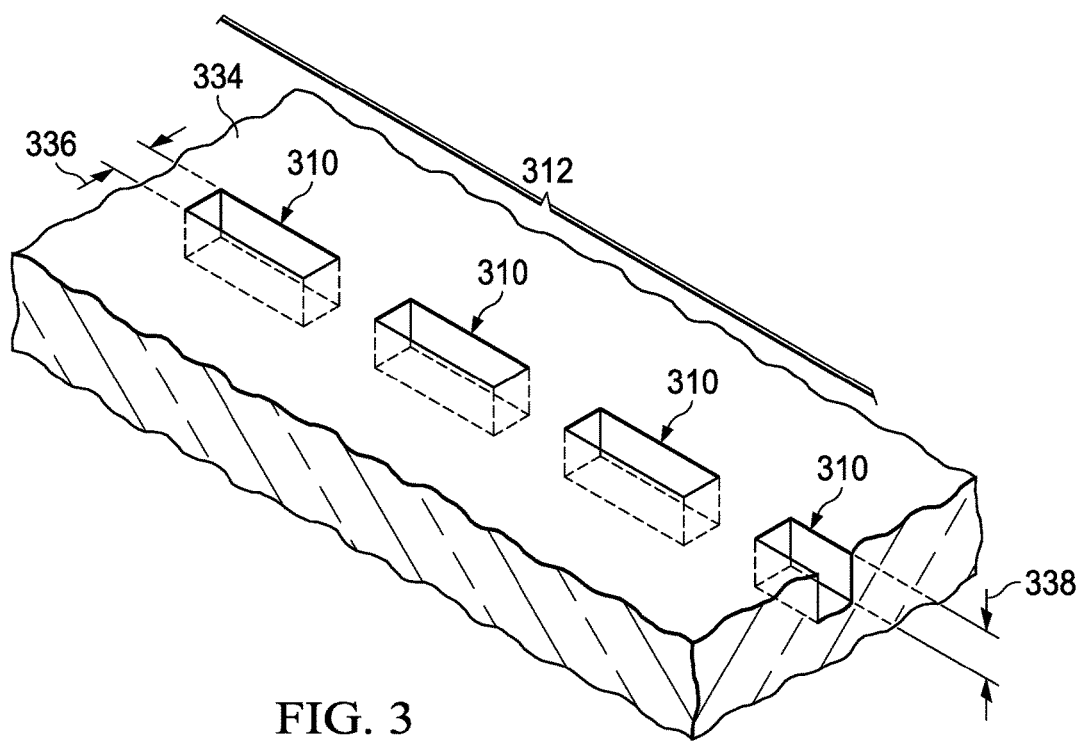
FIG. 3 depicts an example configuration of grooves for a condensation reservoir in a sensor cell.

FIG. 3 depicts an example configuration of grooves for a condensation reservoir in a sensor cell. A structural element 334 of the sensor cell may be, for example, a plate similar to the first plate 102 and/or the second plate 106 described in reference to FIG. 1. Alternatively, the structural element 334 may be an interposer similar to the interposer 104 described in reference to FIG. 1. Further, the structural element 334 may be part of a sensor cell having a different architecture from the sensor cell 100 described in reference to FIG. 1. The structural element 334 has a condensation reservoir 312 which includes a groove 310 having multiple segments in the structural element 334. The segments of the groove 310 are open to an internal sensor volume of the sensor cell. Each of the segments of the groove 310 may have a width 336 less than 1 millimeter, and a depth 338 less than 5 millimeters. Forming the groove 310 as a plurality of segments may advantageously provide a desired degree of mechanical stiffness in the structural element 334 compared to a similar structural element having a continuous groove.

Figure 4:
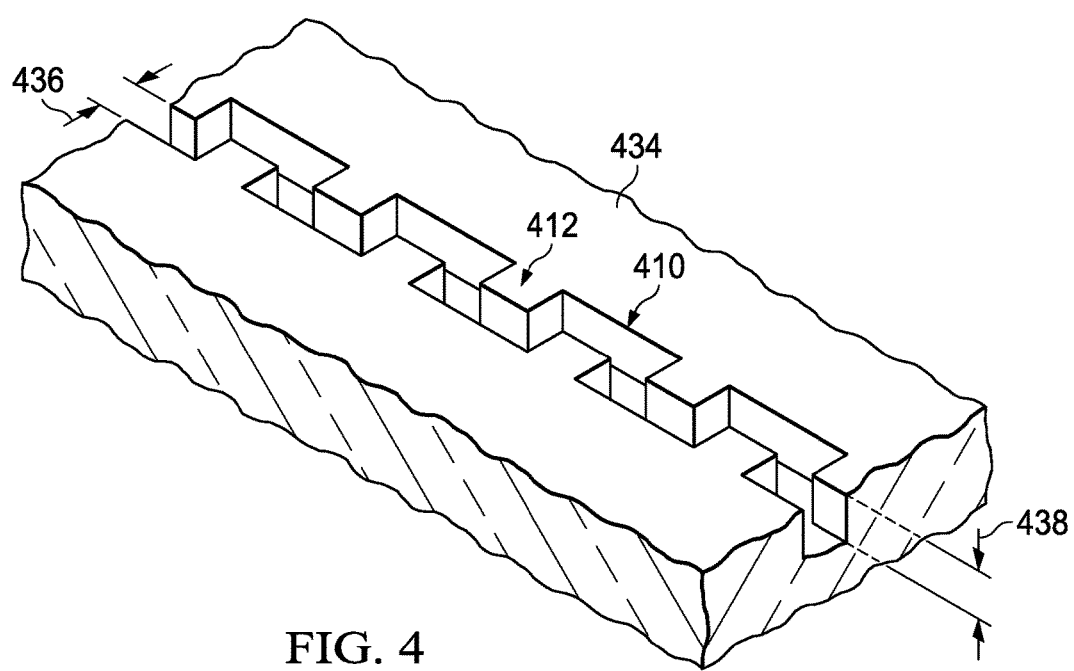
FIG. 4 depicts another example configuration of grooves for a condensation reservoir in a sensor cell.

FIG. 4 depicts another example configuration of grooves for a condensation reservoir in a sensor cell. A structural element 434 of the sensor cell may be, for example, a plate, an interposer or another part of a sensor cell. The structural element 434 has a condensation reservoir 412 which includes a continuous crenelated groove 410 which is open to an internal sensor volume of the sensor cell. The groove 410 may have a width 436 less than 1 millimeter, and a depth 438 less than 5 millimeters. Forming the groove 410 with the crenelated configuration may advantageously provide a desired volume of the condensation reservoir within a desired space.

Figure 5A:
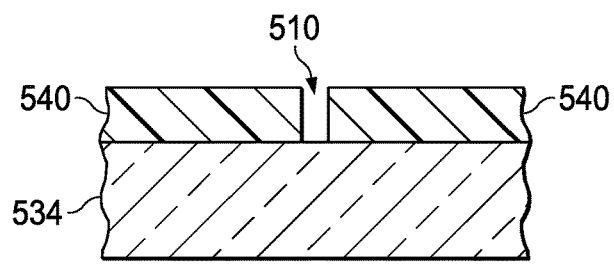
FIG. 5A through FIG. 5D are cross sections of a structural element of a sensor cell, depicted in successive stages of an example method of forming a groove of a condensation reservoir.

FIG. 5A through FIG. 5D are cross sections of a structural element of a sensor cell, depicted in successive stages of an example method of forming a groove of a condensation reservoir. Referring to FIG. 5A, the structural element 534 of the sensor cell may be, for example, a plate, an interposer or another part of a sensor cell. The structural element 534 may be part of a workpiece containing multiple instances of the structural element 534 as described in reference to FIG. 2. A mask 540 is formed on the structural element 534 which exposes an area for a groove 510 which is part of a condensation reservoir of the sensor cell. The mask 540 may include photoresist formed by a photolithographic process, and may include an anti-reflection layer. The mask 540 may include a layer of hard mask material such as amorphous carbon.

Figure 5B:
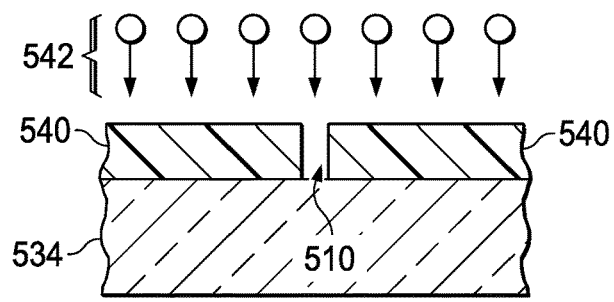

Referring to FIG. 5B, a plasma etch process 542 using vapor phase reactants such as fluorine radicals removes material from the structural element 534 in the area exposed by the mask 540 to form the groove 510 in the structural element 534. The plasma etch process 542 may be a deep reactive ion etch (DRIE) process, which has anisotropic etching characteristics, to provide a desired low undercut of the mask 540. The groove 510 may have a width less than 1 millimeter and a depth less than 5 millimeters. Using a DRIE process to form the groove may advantageously enable forming the depth to be several times greater than the width, desirably providing a higher volume of the groove 510 in a given are of the structural element 534.

Figure 5C:
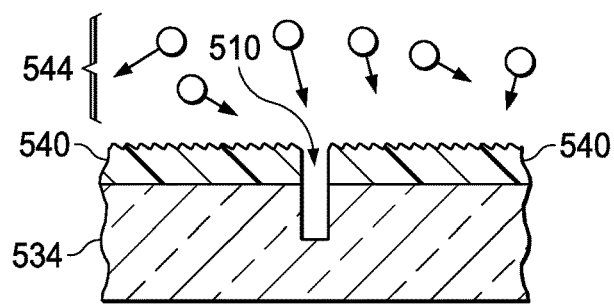

Referring to FIG. 5C, the mask 540 is removed. Organic materials in the mask 540 such as photoresist may be removed by an oxygen ash process 544 as depicted in FIG. 5C. Amorphous carbon in the mask 540 may also be removed by the oxygen ash process 544. The oxygen ash process 544 may provide a hydrophilic surface in the groove 510 which may advantageously promote condensation of a sensor fluid after operation of the sensor cell. Alternatively, organic materials in the mask 540 such as photoresist may be removed by a wet clean process, such as an aqueous mixture of sulfuric acid and hydrogen peroxide, or an aqueous mixture of ammonium hydroxide and hydrogen peroxide.

Figure 5D:
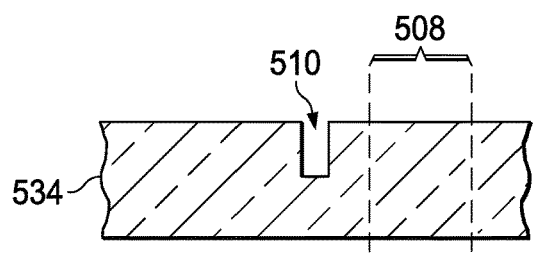

Referring to FIG. 5D, the mask 540 of FIG. 5C is completely removed, leaving the groove 510 in the structural element 534. In versions of the instant example in which a signal path 508 through the sensor cell pass through the structural element 534, the mask 540 is preferably removed so as to avoid degrading signal transmission characteristics of the structural element 534. For example, in versions of the instant example in which the structural element 534 comprises optically transparent material and the signal path 508 is an optical signal path, the mask 540 is preferably removed so as to avoid degrading optical transmission properties, such as surface smoothness, of the structural element 534.

Figure 6A:
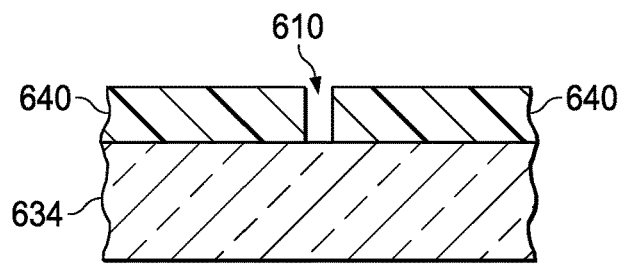
FIG. 6A through FIG. 6D are cross sections of a structural element of a sensor cell, depicted in successive stages of another example method of forming a groove of a condensation reservoir.

FIG. 6A through FIG. 6D are cross sections of a structural element of a sensor cell, depicted in successive stages of another example method of forming a groove of a condensation reservoir. Referring to FIG. 6A, the structural element 634 of the sensor cell may be, for example, a plate, an interposer or another part of a sensor cell. The structural element 634 may be part of a workpiece containing multiple instances of the structural element 634 as described in reference to FIG. 2. A mask 640 is formed on the structural element 634 which exposes an area for a groove 610 which is part of a condensation reservoir of the sensor cell. The mask 640 may be formed similarly to the mask 540 described in reference to FIG. 5A.

Figure 6B:
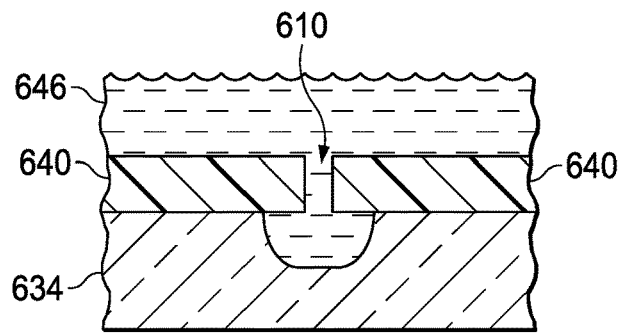

Referring to FIG. 6B, a wet etch process 646 using, for example, an aqueous buffered solution of hydrofluoric acid, removes material from the structural element 634 in the area exposed by the mask 640 to form the groove 610 in the structural element 634. The wet etch process 646 is primarily an isotropic process, undercuts the mask 640. The groove 610 may have a width less than 1 millimeter and a depth less than the width, as a result of the isotropic nature of the wet etch process 646. Using the wet etch process 646 may advantageously provide a desired volume of the groove 610 with a limited depth, for example in a thin structural element 634. The wet etch process 646 may advantageously enable batch processing of multiple workpieces, desirably reducing fabrication cost of the sensor cells containing the structural elements 634.

Figure 6C:
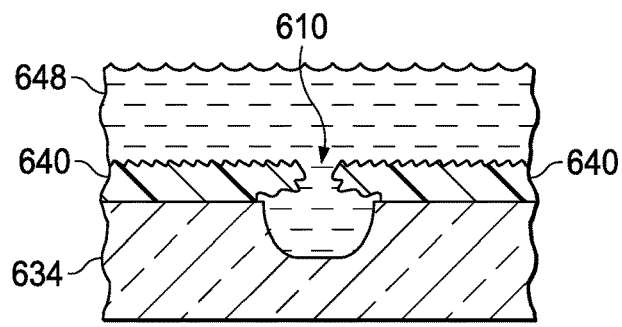

Referring to FIG. 6C, the mask 640 is removed. The mask 640 may be removed by an oxygen ash process, or by a wet clean process 648 as depicted in FIG. 6C, such as an aqueous mixture of sulfuric acid and hydrogen peroxide, or an aqueous mixture of ammonium hydroxide and hydrogen peroxide.

Figure 6D:
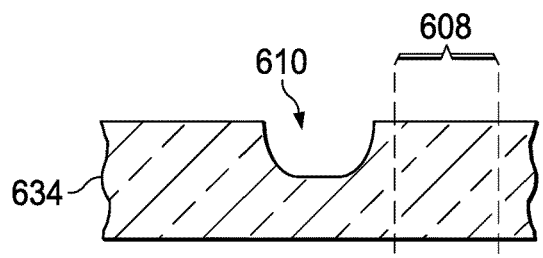

Referring to FIG. 6D, the mask 640 of FIG. 6C is completely removed, leaving the groove 610 in the structural element 634. As disclosed in reference to FIG. 5D, the mask 640 is preferably removed so as to avoid degrading signal transmission characteristics of the structural element 634 where a signal path 608 intersects the structural element 634.

Figure 7A:
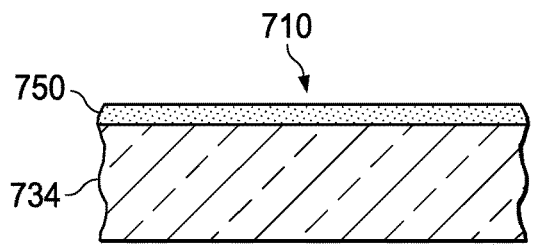
FIG. 7A through FIG. 7D are cross sections of a structural element of a sensor cell, depicted in successive stages of a further example method of forming a groove of a condensation reservoir.

FIG. 7A through FIG. 7D are cross sections of a structural element of a sensor cell, depicted in successive stages of a further example method of forming a groove of a condensation reservoir. Referring to FIG. 7A, the structural element 734 of the sensor cell may be, for example, a plate, an interposer or another part of a sensor cell, and may be part of a workpiece containing multiple instances of the structural element 734. A protective coating 750 is formed on the structural element 734 which covers at least one surface of the structural element including an area for a groove 710 which is part of a condensation reservoir of the sensor cell. The protective coating 750 may be an organic coating, for example a polyisoprene resin or a phenolic resin. The protective coating 750 may be applied, for example, by spin coating or spraying.

Figure 7B:
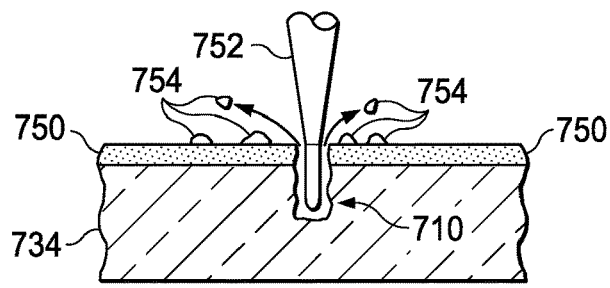

Referring to FIG. 7B, a laser ablation process 752 using, for example, an infrared laser or a visible light laser, removes material from the structural element 734 to form the groove 710 in the structural element 734. The laser may be vector scanned or raster scanned to form the groove 710 with a desired pattern, such as the patterns described in reference to FIG. 1, FIG. 3 and FIG. 4. Using the laser ablation process 752 to form the groove 710 may advantageously provide a flexible patterning process for producing different configurations for multiple instances of the groove 710 with reduced costs compared to masked etch processes. The removed material from the structural element 734 may form debris particles 754 which deposit on the protective coating 750 adjacent to the groove 710. The protective coating 750 advantageously prevents the debris particles 754 from adhering to the structural element 734.

Figure 7C:
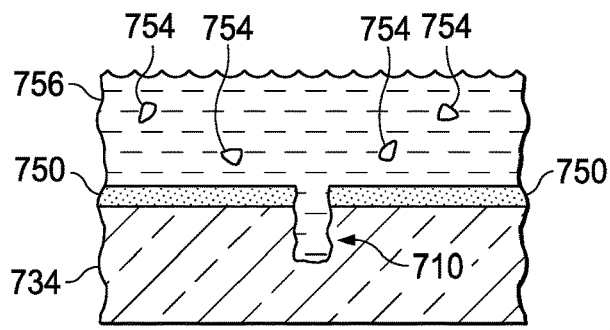

Referring to FIG. 7C, the debris particles 754 are removed, for example by a wet clean process 756. The protective coating 750 may be partially or completely removed by the wet clean process 756. The wet clean process may include, for example, an aqueous mixture of ammonium hydroxide and hydrogen peroxide. Any remaining protective coating 750 may be removed by a solvent clean appropriate for the organic resin in the protective coating 750.

Figure 7D:
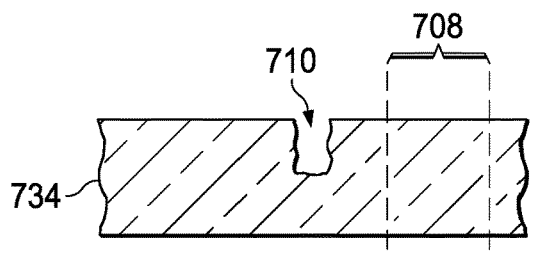

Referring to FIG. 7D, the protective coating 750 of FIG. 7C is preferably removed so as to avoid degrading signal transmission characteristics of the structural element 734 where a signal path 708 intersects the structural element 734. Forming the groove 710 by the laser ablation process may provide a rough surface in the groove 710 which may advantageously promote condensation of a sensor fluid after operation of the sensor cell.

Figure 8:
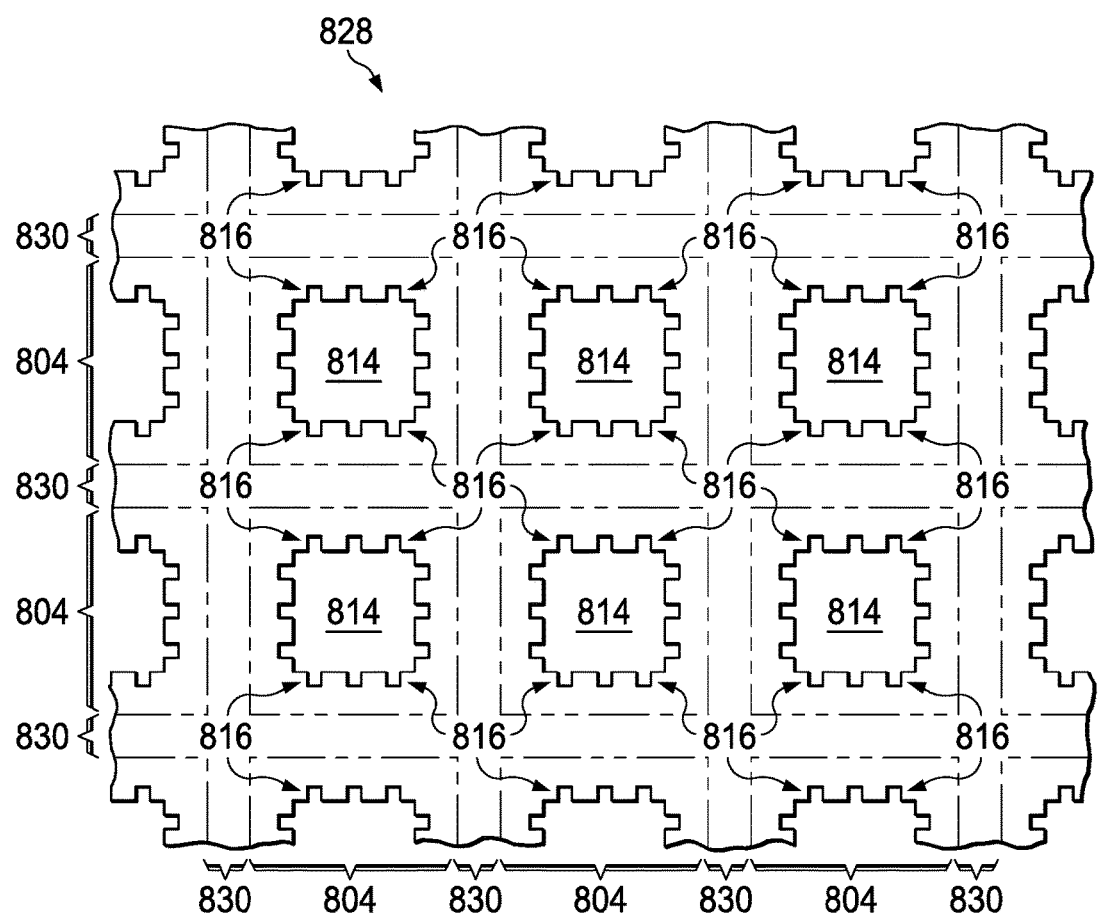
FIG. 8 is a plan view of a plurality of interposers similar to the interposer described in reference to FIG. 1, depicted in an example method of formation.

FIG. 8 is a plan view of a plurality of interposers similar to the interposer 104 described in reference to FIG. 1, depicted in an example method of formation. The plurality of interposers 804 are contained in a workpiece 828, which may be, for example, a circular wafer of silicon, ceramic, glass, sapphire, or quartz, compatible with semiconductor processing equipment. Alternatively, the workpiece 828 may be a square or rectangular substrate of glass, quartz, ceramic or metal, compatible with chip carrier processing equipment. The instances of the interposers 804 are arranged in rows and columns, separated by singulation lanes 830. Each interposer 804 surrounds an opening through the workpiece 828 for an internal sensor volume 814 of the sensor cell. Condensation reservoir grooves 816 are formed in the interposers 804 to be part of condensation reservoirs of sensor cells containing the interposers 804. In the instant example, the condensation reservoir grooves 816 are formed to be open to the openings for the internal sensor volumes 814. The condensation reservoir grooves 816 may be formed concurrently with the openings for the internal sensor volumes 814. Additional openings through the workpiece 828 may optionally be formed in the singulation lanes 830 to assist subsequent singulation of the interposers 804. The interposers 804 are separated from each other by a singulation process such as sawing, mechanical scribing, or laser scribing, through the singulation lanes 830. Forming the interposers 804 in the workpiece 828 may advantageously reduce fabrication costs of the sensor cells containing the interposers 804. A first workpiece containing a plurality of plates, such as described in reference to FIG. 2, may be attached to the workpiece 828 before singulation, to further reduce fabrication costs. Similarly, a second workpiece containing plates may be attached to the workpiece 828 opposite the first workpiece, before singulation, to provide a plurality of the sensor cells, further reducing fabrication costs.

Figure 9A:
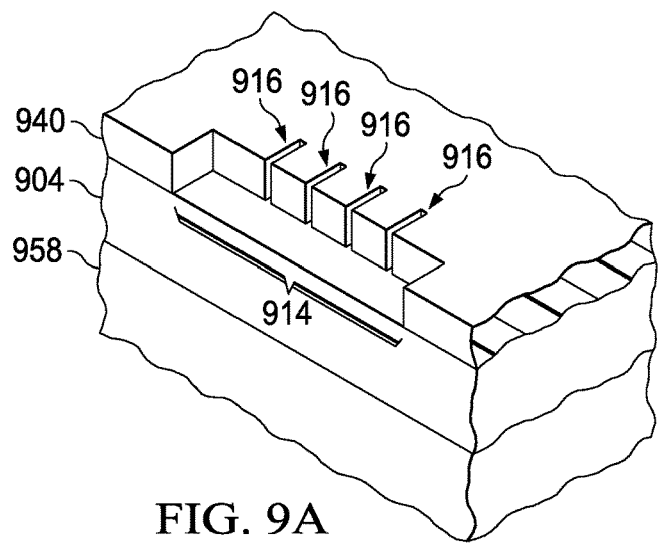
FIG. 9A through FIG. 9D are cross sections of an interposer of a sensor cell, depicted in successive stages of an example method of forming a groove of a condensation reservoir.

FIG. 9A through FIG. 9D are cross sections of an interposer of a sensor cell, depicted in successive stages of an example method of forming a groove of a condensation reservoir. Referring to FIG. 9A, the interposer 904 may be part of a workpiece containing multiple instances of the interposer 904, as described in reference to FIG. 8. The interposer 904 may be mounted on a carrier substrate 958 such as a silicon wafer or ceramic substrate. A mask 940 is formed on the interposer 904 which exposes an area for an opening which provides an internal sensor volume 914 of the sensor cell. In the instant example, the mask 940 includes geometries for grooves 916 around a periphery of the area for the opening which provides the internal sensor volume 914. The mask 940 may include one or more layers of hard mask material for a DRIE process, such as silicon nitride, silicon carbide and/or silicon carbide nitride.

Figure 9B:
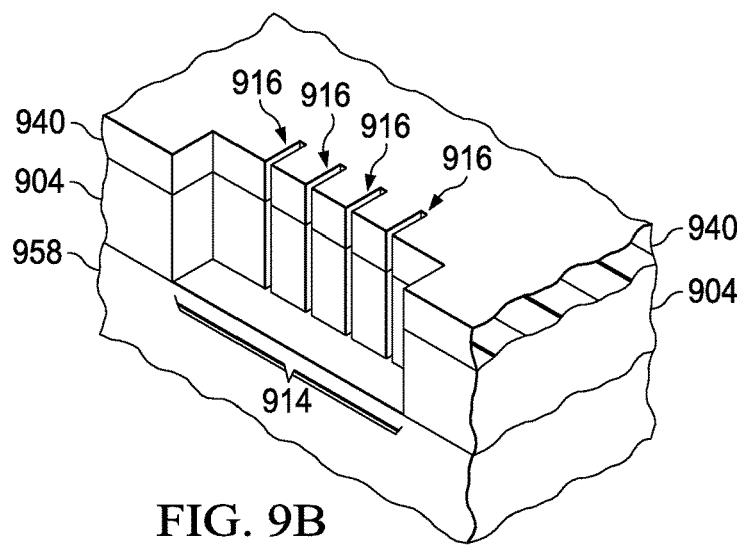

Referring to FIG. 9B, a DRIE process, for example a Bosch etch process, removes material from the interposer 904 in the area exposed by the mask 940 to form the opening for the internal sensor volume 914. The grooves 916 are formed in the interposer 904 around the periphery of the opening for the internal sensor volume 914. Forming the grooves 916 concurrently with the opening for the internal sensor volume 914 may advantageously reduce fabrication cost of the sensor cell. The DRIE process may be endpointed after exposing the carrier substrate 958. The DRIE process may be selective to the carrier substrate 958. Alternatively, the DRIE process may remove material from the carrier substrate 958 in the area exposed by the opening for the internal sensor volume 914.

Figure 9C:
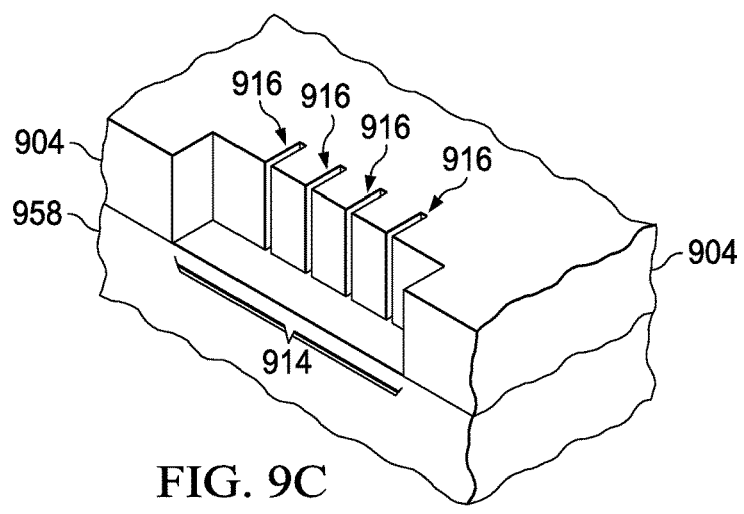

Referring to FIG. 9C, the mask 940 of FIG. 9B is removed. Inorganic materials in the mask 940 such as silicon nitride and silicon carbide may be removed by a plasma etch process which is selective to the material of the interposer 904. Alternatively, inorganic materials in the mask 940 such as silicon nitride may be removed by a wet clean process, such as an aqueous solution of phosphoric acid.

Figure 9D:
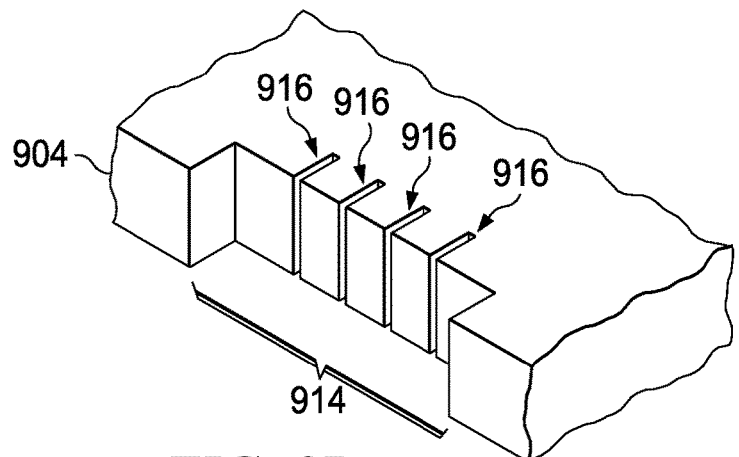

Referring to FIG. 9D, the carrier substrate 958 of FIG. 9C is removed, leaving the interposer 904. In a version of the instant example in which the interposer 904 is part of a workpiece, the carrier substrate 958 may optionally be removed before singulating the interposer 904 from the workpiece. Alternatively, the interposer 904 may be singulated from the workpiece while the carrier substrate 958 is attached, so that the carrier substrate 958 provides a singulation substrate for the workpiece.

Figure 10:
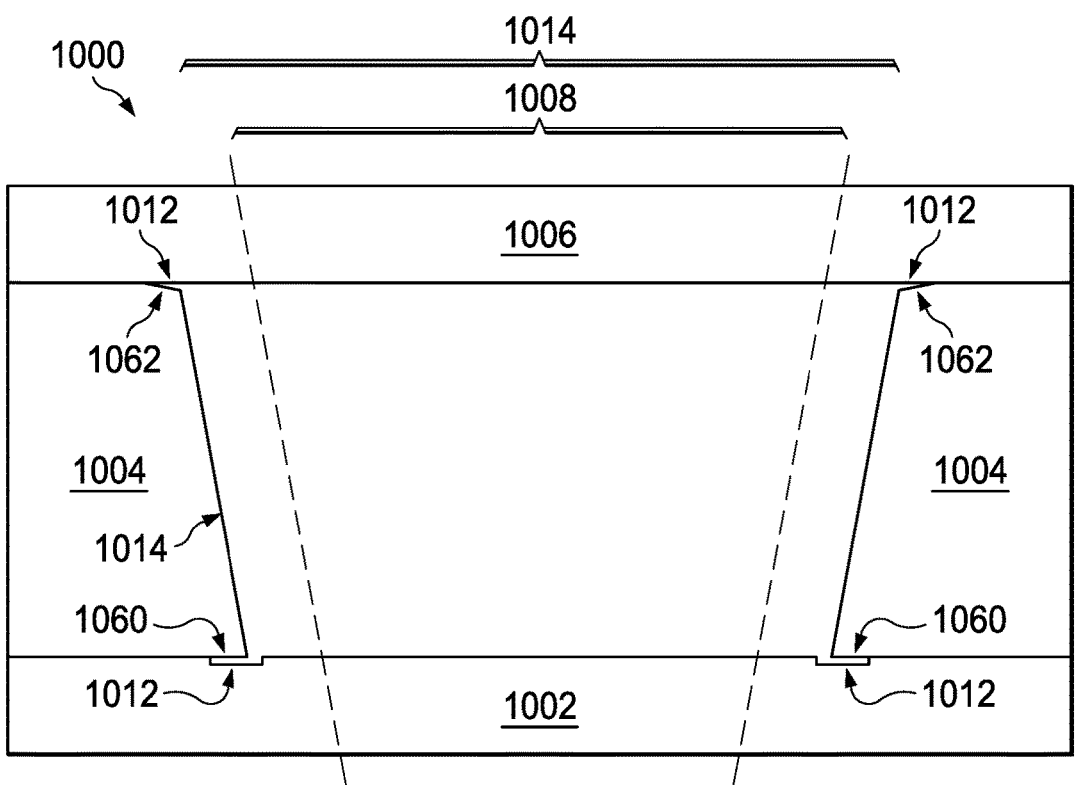
FIG. 10 is a cross section of an example sensor cell with another configuration for a condensation reservoir.

FIG. 10 is a cross section of an example sensor cell with another configuration for a condensation reservoir. The sensor cell 1000 of the instant example includes a first plate 1002 attached to an interposer 1004 and a second plate 1006 attached to the interposer 1004 opposite the first plate 1002. The interposer 1004 may be configured as a closed loop with sloped sides surrounding an internal sensor volume 1014 of the sensor cell 1000; the internal sensor volume 1014 is bounded by the interposer 1004, the first plate 1002 and the second plate 1006. A signal path 1008 extends through the internal sensor volume 1014 and through the first plate 1002 and/or the second plate 1006; the interposer 1004 lies outside of the signal path 1008.

In the instant example, the condensation reservoir 1012 includes a first groove 1060 disposed between the first plate 1002 and the interposer 1004. The first groove 1060 is open to the internal sensor volume 1014 and is disposed outside of the signal path 1008. The first groove 1060 may be formed by forming a recess in the first plate 1002 extending partway under the interposer 1004 and into the internal sensor volume 1014. The first groove 1060 may extend continuously around a perimeter of the internal sensor volume 1014 to provide a desired volume for the condensation reservoir 1012. Alternatively, the first groove 1060 may be segmented, to add mechanical strength to the sensor cell 1000.

In the instant example, the condensation reservoir 1012 also includes a second groove 1062 disposed between the second plate 1006 and the interposer 1004. The second groove 1062 is open to the internal sensor volume 1014 and is disposed outside of the signal path 1008. The second groove 1062 may be formed by forming a recess on the interposer 1004 where the second plate 1006 attached to the interposer 1004. The recess may be in the form of a bevel with varying depth as depicted in FIG. 10, or may be a recess with a constant depth. The second groove 1062 may extend continuously around a perimeter of the internal sensor volume 1014 or may be segmented. A similar sensor cell may have a condensation reservoir consisting of grooves similar to the first groove 1060. Another similar sensor cell may have a condensation reservoir consisting of grooves similar to the second groove 1062. A sensor cell may have a condensation reservoir comprising any combination of grooves similar to the first groove 1060, the second groove 1062, and/or any of the grooves disclosed in the examples herein.

Figure 11A:
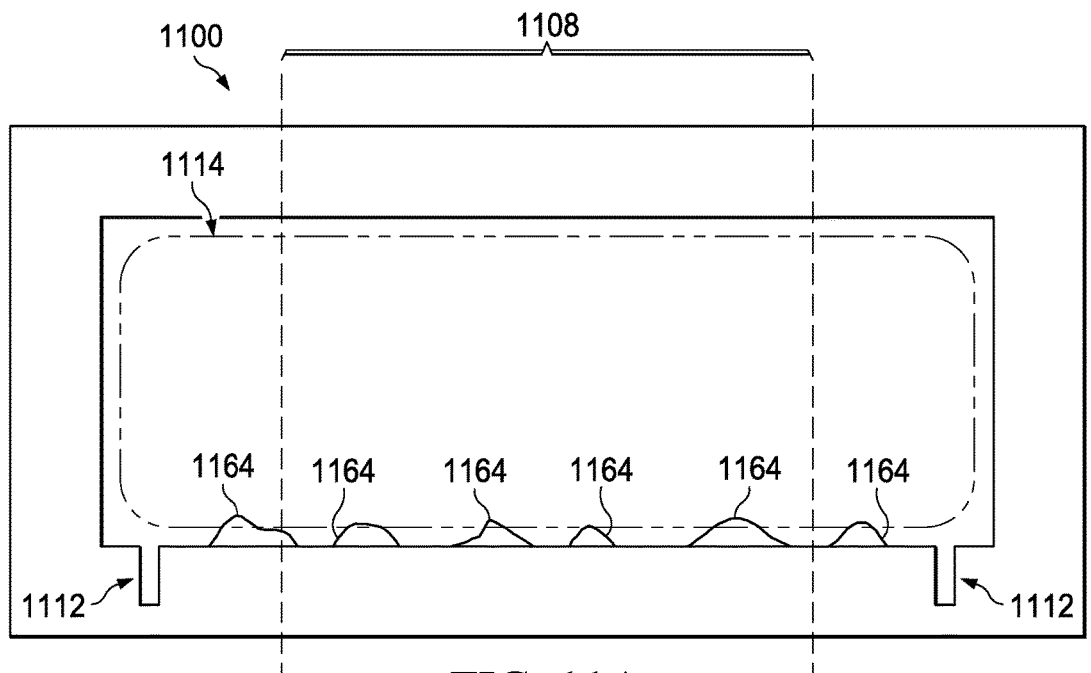
FIG. 11A through FIG. 11D are cross sections of a sensor cell which includes a condensation reservoir, depicted in successive stages of operation.

FIG. 11A through FIG. 11D are cross sections of a sensor cell which includes a condensation reservoir, depicted in successive stages of operation. FIG. 11A depicts the sensor cell 1100 after disposing a condensed phase sensor fluid 1164 in an internal sensor volume 1114 of the sensor cell 1100. The condensed phase sensor fluid 1164 may be, for example, a liquid or solid state of an alkali metal such as cesium or rubidium. The condensed phase sensor fluid 1164 may possibly derive from a sensor precursor substance, such as cesium azide, which produces the condensed phase sensor fluid 1164. There may be a small portion of vapor phase sensor fluid in the internal sensor volume 1114. The condensed phase sensor fluid 1164 may be disposed in a signal path 1108 of the sensor cell 1100. At this stage, relatively little, if any, of the condensed phase sensor fluid 1164 may be disposed in a condensation reservoir 1112 of the sensor cell 1100, located outside of the signal path 1108. The condensation reservoir 1112 may have, for example, any of the configurations disclosed herein.

Figure 11B:
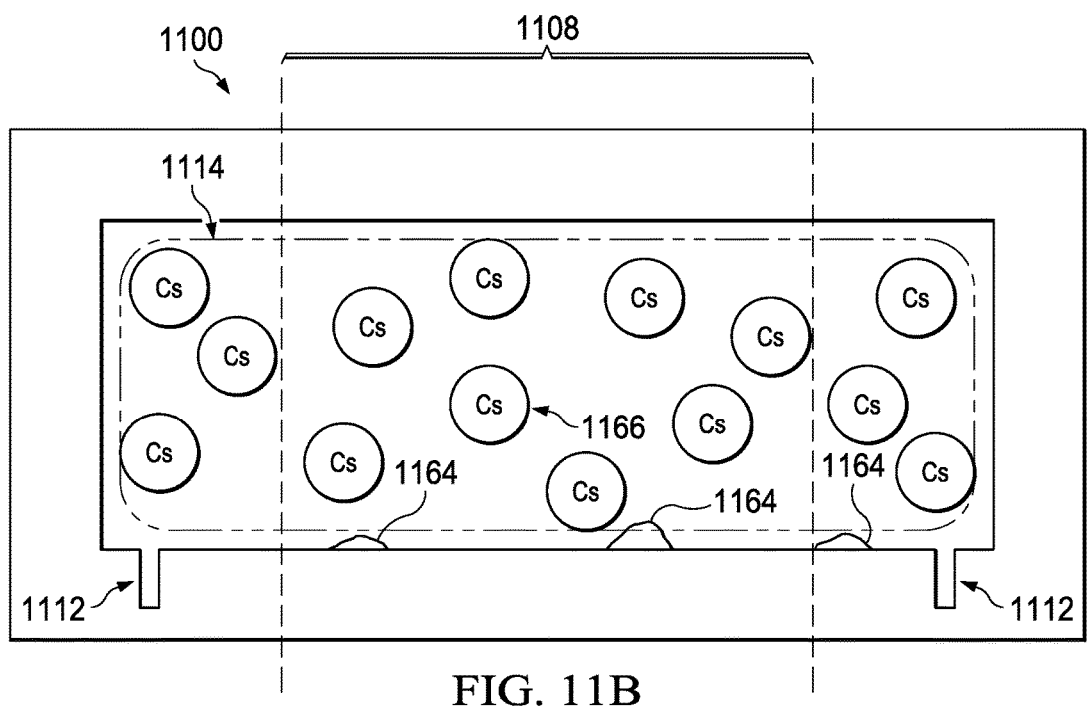

Referring to FIG. 11B, the sensor cell 1100 is subsequently heated so as to convert at least a portion of the condensed phase sensor fluid 1164 to a vapor phase sensor fluid 1166 in the internal sensor volume 1114. The vapor phase sensor fluid 1166 is depicted in FIG. 11B as vapor phase cesium. There may be some condensed phase sensor fluid 1164 remaining in the signal path 1108. Heating the sensor cell 1100 is part of a process to remove the condensed phase sensor fluid 1164 from the signal path 1108 to the condensation reservoir 1112.

Figure 11C:
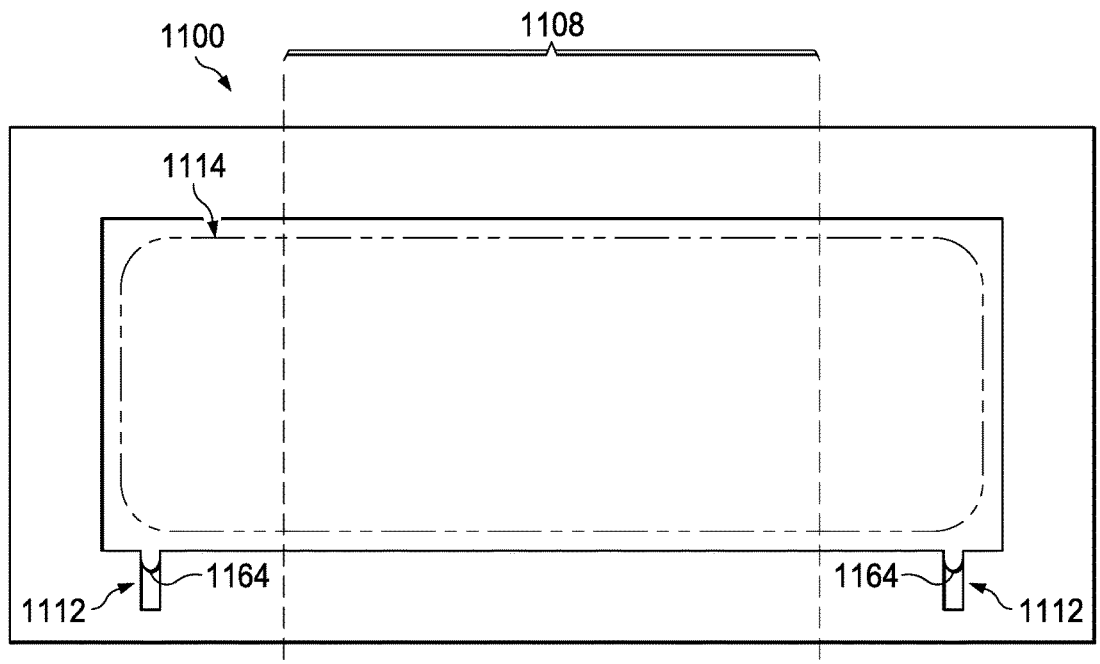

Referring to FIG. 11C, the sensor cell 1100 is subsequently cooled. A significant portion, at least half, of the vapor phase sensor fluid 1166 of FIG. 11B is converted to the condensed phase sensor fluid 1164 which condenses in the condensation reservoir 1112, thus transferring at least a portion of the condensed phase sensor fluid 1164 from the signal path 1108 to the condensation reservoir 1112 located outside of the signal path 1108. The combined steps of heating the sensor cell 1100 as described in reference to FIG. 11B and subsequently cooling the sensor cell 1100 as described in reference to FIG. 11C may be repeated to transfer a desired amount of the condensed phase sensor fluid 1164 from the signal path 1108 to the condensation reservoir 1112. The condensation reservoir 1112 thus provides a means for substantially clearing the signal path 1108 of the condensed phase sensor fluid 1164 and a means for maintaining the signal path 1108 substantially free of the condensed phase sensor fluid 1164.

Figure 11D:
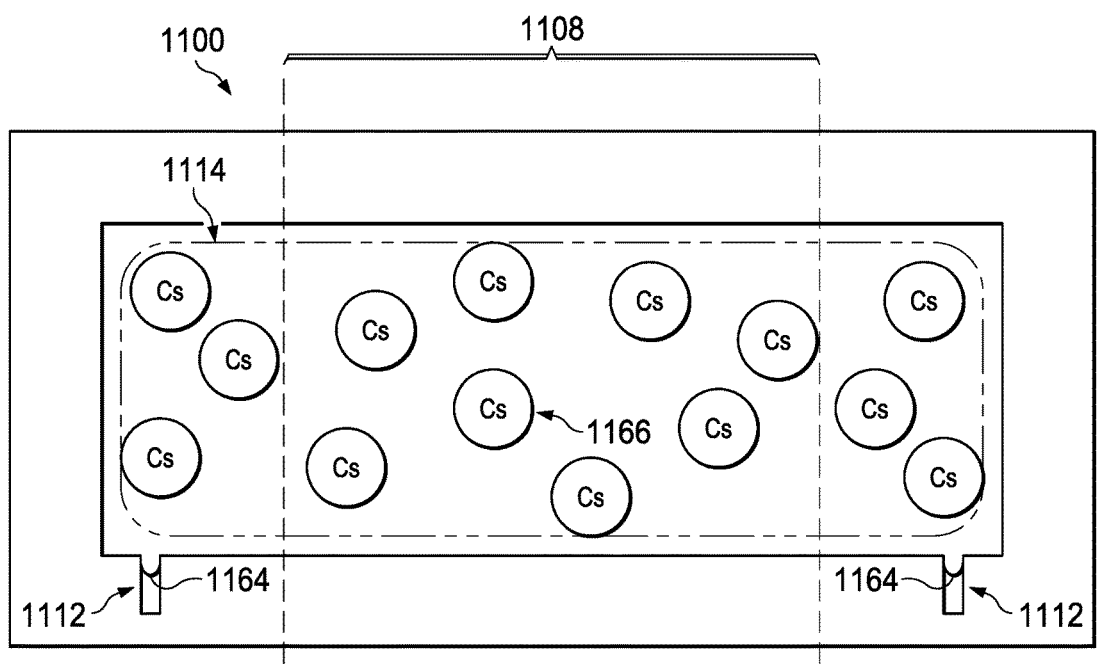

Referring to FIG. 11D, the sensor cell 1100 is operated in a sensing mode by heating the sensor cell 1100 to convert a desired portion of the condensed phase sensor fluid 1164 to the vapor phase sensor fluid 1166 in the internal sensor volume 1114. Some of the condensed phase sensor fluid 1164 may remain in the condensation reservoir 1112. A signal passes through the vapor phase sensor fluid 1166 in the signal path 1108. As a result of the heating and cooling steps described in reference to FIG. 11B and FIG. 11C, the signal path 1108 may be substantially free of the condensed phase sensor fluid 1164, advantageously reducing interference with the signal. After the sensor cell 1100 is operated in a sensing mode, the sensor cell 1100 may be cooled. The vapor phase sensor fluid 1166 may condense in the condensation reservoir 1112, advantageously keeping the signal path 1108 substantially free of the condensed phase sensor fluid 1164.

While various embodiments of the present disclosure have been described above, it should be understood that they have been presented by way of example only and not limitation. Numerous changes to the disclosed embodiments can be made in accordance with the disclosure herein without departing from the spirit or scope of the disclosure. Thus, the breadth and scope of the present disclosure should not be limited by any of the above described embodiments. Rather, the scope of the disclosure should be defined in accordance with the following claims and their equivalents.

What is claimed is:

1. A sensor cell, comprising:
    a chamber defining an internal sensor volume for storing a vapor phase sensor fluid, the internal sensor volume allowing a signal path to extend therethrough with a direction; and
    a condensation reservoir in fluid communication with the internal sensor volume, and the condensation reservoir spatially separated from the signal path and including a plurality of grooves arranged along a perimeter of the chamber, the grooves beginning at a first side of the chamber and ending at an opposite second side of the chamber in the direction of the signal path.

2. The sensor cell of claim 1, wherein the grooves have a width less than 1 millimeter and a depth less than 5 millimeters.

3. The sensor cell of claim 1, further comprising:
    an interposer of the chamber, the interposer laterally surrounding the internal sensor volume;
    a first plate of the chamber, the first plate attached to the interposer; and
    a second plate of the chamber, the second plate attached to the interposer,
    wherein the plurality of grooves includes grooves in the interposer that intersect with grooves in the first plate.

4. The sensor cell of claim 3, wherein the condensation reservoir comprises a first plate groove in the first plate open to the internal sensor volume, the first plate groove having a width less than 1 millimeter and a depth less than 5 millimeters.

5. The sensor cell of claim 4, wherein the first plate groove comprises multiple segments, each segment having a width less than 1 millimeter and a depth less than 5 millimeters.

6. The sensor cell of claim 4, wherein the first plate groove has a continuous crenelated configuration.

7. The sensor cell of claim 4, wherein the condensation reservoir comprises a second plate groove in the second plate open to the internal sensor volume, the second plate groove having a width less than 1 millimeter and a depth less than 5 millimeters.

8. The sensor cell of claim 3, wherein the condensation reservoir comprises a plurality of interposer grooves formed in a surface of the interposer open to the internal sensor volume, the interposer grooves each having a width less than 1 millimeter and a depth less than 5 millimeters.

9. The sensor cell of claim 3, wherein the plurality of grooves includes a plate groove located between the interposer and the first plate, the plate groove being open to the internal sensor volume, the plate groove having a width less than 1 millimeter and a depth less than 5 millimeters.

10. The sensor cell of claim 3, wherein the signal path extends through the first plate and through the second plate.

11. The sensor cell of claim 1, comprising cesium in at least one of the internal sensor volume and the condensation reservoir.

12. A method of forming a sensor cell, comprising:
    forming a condensation reservoir including a plurality of grooves arranged along a perimeter of a chamber and located in one or more of a first plate of the sensor cell, a second plate of the sensor cell, and an interposer of the sensor cell in which the grooves begin at a first side of the chamber and end at an opposite second side of the chamber in a direction from the first plate to the second plate, the interposer laterally surrounding an internal sensor volume;
    attaching the first plate to the interposer, so that at least a portion of the first plate is exposed to the internal sensor volume; and
    attaching the second plate to the interposer, so that at least a portion of the second plate is exposed to the internal sensor volume;
    wherein the first and second plates provide an optical signal path through internal sensor volume, the plurality of grooves being outside the signal path.

13. The method of claim 12, wherein the grooves have a width less than 1 millimeter and a depth less than 5 millimeters.

14. The method of claim 12, further comprising forming a perimeter groove in the first plate.

15. The method of claim 14, further comprising forming sidewall grooves in the interposer by a process that includes a plasma etch process removing a portion of the interposer in a direction normal to the first plate.

16. The method of claim 12, wherein the first plate is contained in a workpiece, the workpiece containing a plurality of first plates, separated by singulation lanes.

17. The method of claim 16, comprising forming singulation assist grooves in the singulation lanes of the workpiece.

18. The method of claim 12, wherein the plurality of grooves includes a sidewall groove formed in the interposer.

19. The method of claim 18, wherein the grooves are formed concurrently with forming the internal sensor volume in the interposer.

20. The method of claim 18, wherein the interposer is contained in a workpiece, the workpiece containing a plurality of interposers, separated by singulation lanes.

21. The method of claim 12, wherein forming the condensation reservoir comprises forming a recess in the first plate where the first plate is attached to the interposer, so that the recess provides a perimeter groove open to the internal sensor volume, the perimeter groove being located between the first plate and the interposer.

22. The method of claim 12, wherein forming the condensation reservoir comprises forming a recess in the interposer where the first plate is attached to the interposer, so that the recess provides a groove open to the internal sensor volume, the groove being located between the first plate and the interposer.

23. The method of claim 12, further comprising placing alkali metal in the internal sensor volume before attaching the second plate to the interposer.

24. A sensor system, comprising:
a signal detector; and
a sensor cell, comprising:
   a chamber defining an internal sensor volume for storing a vapor phase sensor fluid, the internal sensor volume allowing a signal path to extend through; and
   a condensation reservoir in fluid communication with the internal sensor volume, the condensation reservoir spatially separated from the signal path and including a plurality of grooves arranged along a perimeter of the chamber, the grooves beginning at a first side of the chamber and ending at an opposite second side of the chamber in the direction of the signal path.

25. The sensor system of claim 24, comprising a signal source, the signal path extending to the signal source.

26. The sensor system of claim 25, wherein the sensor cell comprises:
   an interposer of the chamber, the interposer laterally surrounding the internal sensor volume;
   a first plate attached to the interposer, wherein at least a portion of the first plate is exposed to the internal sensor volume; and
   a second plate attached to the interposer, wherein at least a portion of the second plate is exposed to the internal sensor volume, the plurality of grooves being located in one or more of the interposer, the first plate, and the second plate.

27. The sensor system of claim 25, wherein the sensor cell comprises an alkali metal in at least one of the internal sensor volume or the condensation reservoir.

28. The sensor system of claim 25, wherein the condensation reservoir is disposed in a path of a portion of signal emissions from the signal source.

29. A method of forming a sensor cell, comprising:
   forming a first plate and a second plate, the first and second plates each being configured to allow an optical signal to propagate therethrough in a direction;
   attaching the first and second plate to an interposer having internal sidewalls, thereby enclosing an internal sensor volume and providing an optical signal path through said internal sensor volume; and
   forming a plurality of grooves in one or more of the first plate, the second plate and the internal sidewalls beginning at a first side of the internal sidewalls and ending at an opposite second side of the internal sidewalls in the direction of the optical signal path, the plurality of grooves being arranged around a perimeter of the internal sensor volume outside said signal path.

30. The method of claim 29, further comprising forming a plurality of sidewall grooves in the interposer, the sidewall grooves abutting a perimeter groove formed in the first plate or the second plate.

31. The method of claim 30, wherein the sidewall grooves are formed by an etch process that removes a portion of the interposer in a direction parallel to a surface of the internal sidewalls.

* * * * *